United States Patent [19] [11] 4,261,922
Kem [45] Apr. 14, 1981

[54] PROCESS FOR ALKOXYLATION OF PHENOLS

[75] Inventor: Kenneth M. Kem, San Juan Capistrano, Calif.

[73] Assignee: The Dow Chemical Company, Midland, Mich.

[21] Appl. No.: 60,944

[22] Filed: Jul. 26, 1979

[51] Int. Cl.$^3$ .............................................. C07C 41/16
[52] U.S. Cl. ................................ 260/512 R; 568/640; 568/648; 568/638; 568/49; 568/34; 568/315; 568/33; 568/39; 568/48; 564/433
[58] Field of Search ............... 568/648, 638, 649, 640, 568/49, 34, 315, 109, 33; 260/512 R; 564/433

[56] References Cited

U.S. PATENT DOCUMENTS

| | | | |
|---|---|---|---|
| 2,075,018 | 3/1937 | Bruson et al. | 568/648 |
| 2,448,767 | 9/1948 | Carlson | 568/662 X |
| 3,354,227 | 11/1967 | Katzschmann | 568/648 X |

OTHER PUBLICATIONS

Yoshino et al., Bull. Chem. Soc. Japan 47 (1973) 553–556.
Shapiro et al., J. of Chem., U.S.S.R., 5 200 (1968).

*Primary Examiner*—Bernard Helfin
*Attorney, Agent, or Firm*—Douglas N. Deline

[57] ABSTRACT

Hydroxyalkylphenyl ether compounds are prepared by reaction of cyclic organic carbonate compounds with phenols in the presence of potassium iodide catalyst.

6 Claims, No Drawings

PROCESS FOR ALKOXYLATION OF PHENOLS

BACKGROUND OF THE INVENTION

The present invention relates to a process for the preparation of hydroxyalkylphenyl ether compounds. More particularly, the present invention is concerned with an improved catalyst for use in the preparation of hydroxyalkylphenyl ether compounds by the reaction of cyclic organic carbonate compounds with phenols.

Carlson disclosed in U.S. Pat. No. 2,448,767 a method of hydroxyethylation wherein ethylene carbonate or ethylene sulfite was reacted with certain organic compounds including phenols and alcohols. The reaction could be carried out in the presence or in the absence of a suitable solvent, and in the presence or in the absence of a suitable catalyst. Catalysts that were disclosed included an acid (concentrated sulfuric acid or an alkyl ester of sulfuric acid), a base (alkali carbonates), or the alkali salt of a phenol. The preferred catalyst was an alkali carbonate or alkali salt of a phenol. U.S. Pat. No. 3,283,030 disclosed the use of potassium carbonate as a basic catalyst in the reaction of ethylene carbonate with certain substituted phenols.

Alkali metal hydrides disclosed by U.S. Pat. Nos. 2,987,555 and 2,967,892 have also been found to be effective catalysts for alkoxylation reactions of ethylene carbonate with phenols and chloromethylethylene carbonate with phenols respectively.

One disadvantage associated with prior art processes using acidic or basic catalysts has been the occurrence of secondary reactions between the hydroxyalkylphenyl ether product and the carbonate reactant forming quantities of undesirable side-products. A further disadvantage of known prior art processes is the inability to use certain modified phenolic compounds that are unstable under acidic or basic reaction conditions.

SUMMARY OF THE INVENTION

This invention comprises an improved process for the alkoxylation of phenols providing high yields with good selectivity. In particular the invention comprises the use of potassium iodide as a reaction catalyst for the reaction of phenols and cyclic organic carbonate compounds. The ability to operate at a neutral pH according to the invention allows the reaction to be run under relatively mild conditions thereby allowing utilization of reactants having a greater variety of functionality than has been possible under prior known methods. It is also possible utilizing the invented process to attain reaction conditions conducive to exclusive monohydroxyalkoxylation of the phenol reactant. The hydroxyalkylphenyl ether products formed according to this invention are used as solvents and in certain coatings as well as in additional industrial applications.

DETAILED DESCRIPTION OF THE INVENTION

This invention lies in the discovery that potassium iodide acts as an effective catalyst in the reaction of cyclic organic carbonate compounds with phenols.

The catalyst is employed in a catalytically effective amount. Advantageously, the amount of potassium iodide catalyst employed may very compared to total reactant weight from about 0.05 percent to about 10.0 percent. It is preferred to employ the catalyst in amounts from about 0.5 percent to about 2.0 percent by weight.

Phenol reactants suitable for use according to this invention include hydroxy benzene derivatives such as benzene having from 1 to 4 hydroxy substituents and such compounds substituted with from 1 to 5 alkyl, aryl, alkaryl, chloro or combinations of alkyl, aryl, alkaryl or chloro substituents; aliphatic or aromatic compounds substituted with one or more hydroxy phenyl substituents, each hydroxyphenyl substituent containing from 1 to 4 hydroxy groups; hydroxy phenyl substituted bridged aromatic compounds of the formula

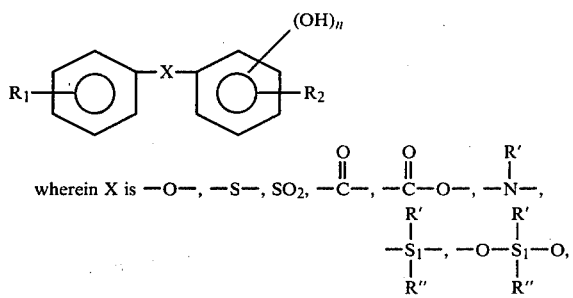

wherein X is $-O-$, $-S-$, $SO_2$, $-\overset{O}{\underset{\|}{C}}-$, $-\overset{O}{\underset{\|}{C}}-O-$, $-\underset{\underset{R'}{|}}{\overset{\overset{R'}{|}}{N}}-$, $-\underset{\underset{R''}{|}}{\overset{\overset{R'}{|}}{Si}}-$, $-O-\underset{\underset{R''}{|}}{\overset{\overset{R'}{|}}{Si}}-O$, n is an integer from 1 to 6 and $R_1$, $R_2$, $R'$ and $R''$ are hydrogen alkyl or aryl; metal salts of phenol sulfonic acid; and mixtures thereof. Preferred phenol reactants are hydroxy benzene derivatives.

However, Tsuruya disclosed in *J. Polymer Science*, Part B, 7, 709 (1969) that 2,4,6-tribromophenol, preferably forms polymers through debromination when reacted with organic carbonate compounds. This compound therefore is not considered to be suitable for use according to the present invention.

The cyclic organic carbonates used in the hydroxyalkylation reactions according to this invention may likewise be varied. In addition to ethylene carbonate, Davis in U.S. Pat. No. 2,987,555 disclosed that any cyclic alkylene carbonate having the appropriate carbonate moiety attached at adjacent positions was capable of undergoing hydroxyalkylation with phenolic compounds. Specifically mentioned carbonate compounds were propylene carbonate, 1,2- or 2,3-butylene carbonate and phenylethylene carbonate. For said disclosure I do incorporate this teaching by reference. A preferred cyclic organic carbonate reactant is ethylene carbonate.

As previously mentioned, use of the potassium iodide as a catalyst at a neutral pH in the practice of this invention instead of strong acidic or basic catalysts advantageously permits the use of reactants containing greater functionality than has been previously possible. The potassium iodide catalyst and milder reaction conditions additionally allow greater selectivity in product formation including the exclusive formation of the monohydroxyalkoxylated product without concomitant formation of secondary reaction products.

The reaction preferably takes place in the absence of an inert solvent although such a solvent may be employed if desired. In the preferred embodiment the cyclic carbonate reactant is a suitable solvent.

The reactants may be combined in nearly any molar ratio since some product is produced under nearly all conditions. It is preferred however, to combine the reactants in a stoichiometric ratio thereby eliminating the need to remove excess reactants from the finished product in a subsequent purification step.

The reaction may be carried out in any vessel suitably designed to contain the reactants and products and be unreactive under the conditions of the invention. Representative of suitable reaction vessels are those made of glass, stainless steel or other unreactive material.

The reaction may be run in the practice of this invention at any suitable temperature from about 100° C. to about 210° C. Faster reaction rates are observed at higher temperatures but decomposition of reactants and products is likely to occur at the higher temperatures. The optimum temperature for particular reactants allowing fast reaction rates, but minimizing decomposition side-products may be easily determined according to ordinary techniques of experimentation. The preferred operating temperature for most phenolic and carbonate reactants is from about 150° C. to about 170° C. Heating the reaction vessel to the operating temperature may conveniently be occasioned by any usual means such as a heat lamp, heating mantle, oil bath, etc.

The time for the reaction to proceed to substantial completion will vary depending on various factors such as the particular phenol-containing reactant, and cyclic organic carbonate reactant. Generally, about two hours to above five hours is sufficient. The evolution of carbon dioxide is a convenient indicator of the progress of the reaction.

The reaction may be run accompanied by either mechanical or magnetic stirring or without stirring. To avoid liquid entrapment during the evolution of carbon dioxide it is advantageous to employ a condenser according to well-known techniques in the art.

The product, a corresponding hydroxyalkyl ether derivative of the phenol-containing reactant used, may be easily recovered from the reaction mixture, for example, by distillation if a liquid, or by recrystallization if a solid.

While the invention has been described as useful in a batch process reaction, there is no known reason why it may not be utilized equally advantageously in a continuous reaction process.

The catalyst of this invention may also be advantageously employed by being supported by a suitably chosen inert substrate such as silica or alumina, thus aiding in the recoverability of the catalyst from the reaction mixture.

SPECIFIC EMBODIMENTS OF THE INVENTION

Having described the invention the following examples are given merely as illustrative of the present invention and are not to be considered as limiting.

EXAMPLE 1

2-hydroxyethyl phenyl ether

A solution composed of phenol (94.11 g, 1 mole), ethylene carbonate (89.9 g, 1 mole 98 percent purity) and potassium iodide (1 g) placed in a round bottom glass flask was mechanically stirred and flushed with nitrogen. Heating was commenced and at about 110° C. evolution of $CO_2$ (monitored by a bubbler) was observed. Stirring was continued and the temperature maintained at 150° C. until $CO_2$ evolution subsided (approximately 3 hours).

After cooling the flask contained a yellow oil weighing 138.6 g. Distillation gave 135.0 g (97.7 percent yield) of a colorless oil having a boiling point range from 128° C.–130° C. (20 mm), $N_d^{20}=1.5355$. Analysis by gas liquid chromatograph also confirmed the identity of the product as 2-hydroxyethyl phenyl ether.

EXAMPLE 2

Reaction of ethylene carbonate with bisphenol A

Parabisphenol A (228.3 g, 1 mole), ethylene carbonate (179.8 g, 2 moles) and potassium iodide (2 g) were introduced into a round bottom glass flask equipped with a bubbler, a condenser and a mechanical stirrer. The flask was flushed with nitrogen and heated to about 80° C. whereupon the contents melted and stirring commenced. At 120° C. evolution of $CO_2$ was observed. The reaction was maintained at 150° C. for 4 hours. After $CO_2$ evolution subsided the flask and contents were cooled.

An off-white crystalline solid (310 g, 98 percent yield) was obtained. Recrystallization from a mixture of toluene and ethanol yielded 291 g of 2,2-bis[4-(2-hydroxyethoxy)phenyl]propane. A subsequent recrystallization from chloroform yielded colorless crystals having a melting point of 110° C.–111° C.

EXAMPLE 3

Reaction of ethylene carbonate with phenol sulfonic acid sodium salt

A mixture of the sodium salt of p-phenol sulfonic acid (109.9 g, 0.52 mole), ethylene carbonate (46.2 g, 0.52 mole) and 1 g of potassium iodide was stirred in an apparatus as described in the previous examples. At 120° C. the mixture formed a cloudy melt and stirring was commenced. $CO_2$ evolution began immediately. After reaction for 4 hours at 160° C. $CO_2$ evolution subsided. After cooling a solid was obtained and recrystallized from 80 percent ethanol. Yield equaled 83.2 g or 67%. The product had a melting point greater than 315° C. and was soluble in water. A nuclear magnetic resonance spectrum of the product was consonant with that expected of pure sodium 4-(2-hydroxyethoxy)benzene sulfonate.

EXAMPLE 4

Reaction of ethylene carbonate with 2-hydroxy-4-tertiary butyl phenol

A fresh supply of 2-hydroxy-4-tertiary butyl phenol was obtained by recrystallization from pentane. 38.7 g (0.233 mole) of this compound, 41 g (0.47 mole) of ethylene carbonate and 0.1 g of potassium iodide were combined under the reaction conditions used in Example 1. $CO_2$ evolution was observed to commence at 125° C. The reaction was continued with stirring for 4 hours at 150° C. until $CO_2$ evolution subsided.

An amber colored oil (58.5 g, 98.8 percent yield) that solidified upon cooling was isolated. Recrystallization from hexane produced 41.1 g of an off-white solid having a melting point range from 71.5° C.–72.5° C. Analysis by nuclear magnetic resonance spectoscopy confirmed the product was 1,2-di(2-hydroxyethoxy)-4-tertiary butyl benzene.

What is claimed is:

1. In the method of alkoxylation wherein phenol-containing compounds are reacted with cyclic organic carbonate compounds in the presence of a catalyst followed by recovery of the hydroxyalkyl aryl ether formed, the improvement wherein the reaction is conducted without the addition of strong acid or base and the catalyst is potassium iodide.

2. The process of claim 1 wherein the phenol-containing compound and organic carbonate compound are combined in substantially stoichiometric quantities.

3. The process of claim 1 wherein the reaction is carried out at a temperature from about 100° C. to about 210° C.

4. The process of claim 1 wherein the quantity of catalyst present based on total reactant weight is from about 0.05 to about 10 weight percent.

5. The process of claim 1 wherein the cyclic organic carbonate compound is ethylene carbonate.

6. The process of claim 4 wherein the phenol-containing compound is selected from a group consisting of phenol, parabisphenol A, the alkali metal salt of phenol sulfonic acid, and 2-hydroxy-4-tertiary butyl phenol.

* * * * *

UNITED STATES PATENT AND TRADEMARK OFFICE
CERTIFICATE OF CORRECTION

PATENT NO. : 4,261,922

DATED : April 14, 1981

INVENTOR(S) : Kenneth M. Kem

It is certified that error appears in the above—identified patent and that said Letters Patent is hereby corrected as shown below:

Col. 1, line 66, "very" should read --vary--.

Col. 3, line 26, "above" should read --about--.

Signed and Sealed this

First Day of September 1981

[SEAL]

Attest:

GERALD J. MOSSINGHOFF

Attesting Officer     Commissioner of Patents and Trademarks